United States Patent [19]

Gardner

[11] Patent Number: 5,434,259
[45] Date of Patent: Jul. 18, 1995

[54] PROCESS FOR ISOLATION OF CEFACLOR AFTER ENZYMATIC ACYLATION

[75] Inventor: John P. Gardner, Indianapolis, Ind.

[73] Assignee: Eli Lilly and Company, Indianapolis, Ind.

[21] Appl. No.: 14,015

[22] Filed: Feb. 5, 1993

[51] Int. Cl.$^6$ ............................................. C07D 501/12
[52] U.S. Cl. ................................................... 540/215
[58] Field of Search ................................. 540/222, 215

[56] References Cited

U.S. PATENT DOCUMENTS 3,676,434  7/1972  Massey ................................ 260/243
3,816,253  3/1972  Takahashi et al. ..................... 195/29

FOREIGN PATENT DOCUMENTS 0341991  5/1989  European Pat. Off. .

OTHER PUBLICATIONS

Kang, et al., 7(1987), Purification and Catalytic Properties of Cephalexin Synthesizing Enzyme from *Acetobacter turbidans*, Kor. J. Appl. Microbiol. Bioeng. 15(3): 203–208.

*Primary Examiner*—Nicholas Rizzo
*Attorney, Agent, or Firm*—Janet T. McClain; James J. Sales; Gerald V. Dahling

[57] ABSTRACT

Provided is a process for isolating cefaclor from an acylation reaction mixture by adding anthraquinone-1,5-disulfonic acid to the mixture. The acid highly selectively precipitates with cefaclor so that isolation and recovery is streamlined.

9 Claims, No Drawings

PROCESS FOR ISOLATION OF CEFACLOR AFTER ENZYMATIC ACYLATION

FIELD OF THE INVENTION

The present invention relates to an industrially advantageous process for the isolation of cefaclor from the enzymatic acylation reaction mixture by precipitating the cefaclor from the mixture as a 2:1 salt with anthraquinone disulfonic acid.

BACKGROUND OF THE INVENTION

An enzymatic process for the preparation of cephalosporins by condensation of an amino acid derivative and a 7-amino cephalosporin nucleus is described in U.S. Pat. No. 3,816,253. In U.S. patent application Ser. No. 07/874,257 filed Apr. 24, 1992, now abandoned, an improved enzymatic process for preparing cephalosporins is disclosed, particularly relating to condensing the corresponding 7-amino cephalosporin nucleus with an amino acid. Heretofore, after such enzymatic acylation reaction, the compound of interest, cefaclor, is in a complex environment which contains not only the nucleus but also phenylglycine, D-phenylglycinemethyl ester, and salts thereof. In light of the complexity of this mixture, the cefaclor has been isolated by a series of columns. Of course, this results in loss of product and is also time consuming.

In view of the above, what is needed in the art is a process for selectively removing the cefaclor from the complex acylation reaction mixture.

SUMMARY OF THE INVENTION

It has now been found that it is possible to selectively isolate cefaclor or salt thereof from an enzymatic acylation reaction mixture which includes the nucleus, phenylglycine, and D-phenylglycinemethyl ester, and salts thereof, by subjecting the enzymatic acylation reaction mixture to anthraquinone-1,5-disulfonic acid or alkali metal salt thereof. While the anthraquinone disulfonic acid will form salts with the other compounds listed above, the addition of the acid selectively precipitates the cefaclor 2:1 salt formed with anthraquinone-1,5-disulfonic acid from the enzymatic reaction mixture, thus providing an efficient, less time-consuming process for isolating cefaclor from the enzymatic acylation reaction mixture. It is surprising how highly selectively the cefaclor/acid salt precipitates from the mixture. The cefaclor/acid salt itself is described in European Patent Application 341,991, published Nov. 15, 1989.

DESCRIPTION OF THE INVENTION

The process of the invention can be used to isolate cefaclor or salt thereof of the Formula I below:

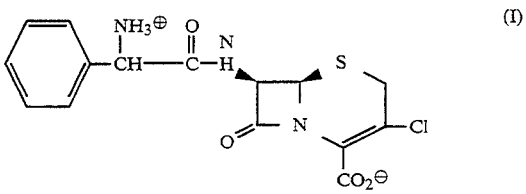

The enzymatic process proceeds as outlined in Scheme I:

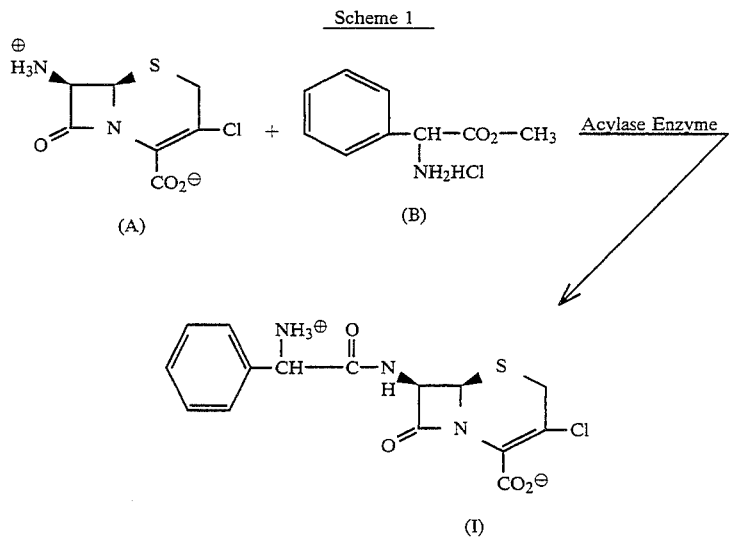

The acylase enzyme used in the enzymatic process may be derived from any of the known microbial sources. Among these are the micro-organisms of the following: Xanthomonas, Pseudomonas, Aeromonas, Escherichia, Arthrobacter, Corynebacterium, and Bacillus genera. The use of penicillin acylase derived from *Escherichia Coli* ATCC 9637 is preferred.

The enzymatic acylation and the subsequent isolation is carried out in an aqueous system. However, suitable organic solvents may be used and include ethylene glycol, lower alcohols (e.g., methanol, ethanol, isopropanol, 2-butanol), acetone and the like. The enzymatic acylation can be run at temperatures as described in the art, and the subsequent precipitation/isolation step can be carried out at temperatures of between about 0° to about 25° C. The preferred temperature range is from 0° to 10° C.

The anthraquinone-1,5-disulfonic acid is added to the acylation reaction mixture in an amount of between about 0.5 moles to about 2 moles per mole of cefaclor to be isolated. A preferred molar amount is between 0.5 moles and 0.7 moles of the acid per mole of cefaclor to be isolated. The acid may be in the form of an alkali metal salt (sodium or potassium).

The precipitation/isolation step may be carried out at a pH of between about 1.0 to about 4.0. A preferred pH range is from about 1.3 to about 1.7. The pH may be controlled by the addition of an appropriate acid, such as hydrochloric acid and/or base such as triethylamine.

After isolation of the cefaclor/acid salt, cefaclor monohydrate may be formed by known procedures. For example, the salt may be dissolved in a DMF/water mixture, and the mixture pH may be raised to about 5.7 to crystallize the cefaclor DMF solvate therefrom. Thereafter, the DMF solvate may be added to water at a low pH (0.5–1.0) to dissolve the mixture, and the cefaclor monohydrate crystallized therefrom at pH 3.5.

The following illustrates the invention.

Preparation 1

7-(D-2-ammonium-2-phenylacetamido)-3-chloro-3-cephem-4-carboxylate, inner salt

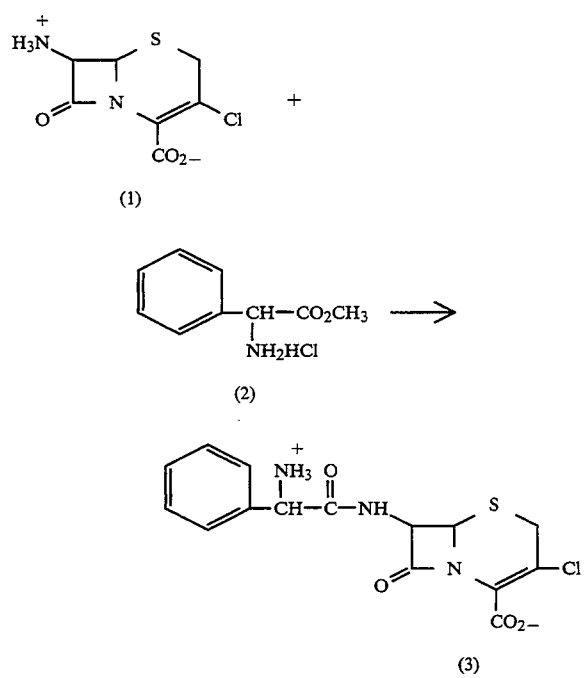

7-ACCA (1) (0.9388 g, 4.0007 mmol) and 96.0 ml of $H_2O$ are combined in a beaker. The pH is 4.12. Three molar $NH_3$ (1.78 ml) is added to the beaker. The pH is 7.57. D-phenylglycinemethyl ester hydrochloride (2) (4.7594 g, 23.602 mmol) is added to the beaker. The pH is 5.68. The mixture is cooled to 5° C., and three molar $NH_3$ (1.90 ml) is added to the mixture to raise the pH to 7.00. Enzyme (6.1442 g, 940 IU/g of nucleus) is added. The following reaction rate data, via HPLC analysis, is provided:

| Time (Min) | pH | Temp (°C.) | Compound 1 % remaining | Compound 2 % remaining | Compound 3 % formed |
|---|---|---|---|---|---|
| 0 | 7.00 | 6 | 100 | 100 | — |
| 85 | 6.28 | 5 | 9.2 | 67.1 | 91.4 |
| 120 | 6.16 | 4 | 9.1 | 64.3 | 91.5 |
| 180 | 5.97 | 4.5 | 8.9 | 63.7 | 91.8 |
| 200 | 5.91 | 4.5 | 8.8 | 65.3 | 93.0 |

At time=200 minutes, the mixture is filtered (to remove the immobilized enzyme) with an in size yield of the titled product being 93%.

Example 1

7-(D-2-ammonium-2-phenylacetamido)-3-chloro-3-cephem-4-carboxylate, inner salt

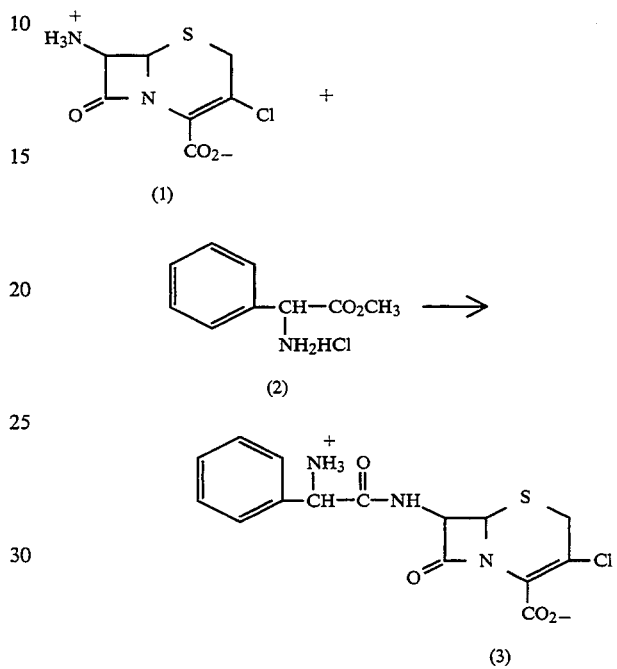

A. Acylation (1) 7-ACCA (1) (4.8338 g, 20 mmol) and 150 ml of $H_2O$ are combined in a beaker. The pH is 3.67. Three molar $NH_3$ (8.40 ml) is added to the beaker. The pH is 8.20. D-phenylglycinemethyl ester hydrochloride (2) (23.0 g, 114 mmol) is added to the beaker. The pH is 5.29. The mixture is filtered through a hyflofilter and washed with 10.0 ml of $H_2O$. The volume of the mixture is 310 ml. The mixture is transferred to a larger beaker and 5 ml $H_2O$ rinse is used. The mixture is cooled to 1° C., and three molar $NH_3$ (16.6 ml) is added to the mixture to raise the pH to 7.28. Enzyme (15.34 g, 500 IU/g of nucleus) is added. The reaction mixture is filtered after 145 minutes to remove enzyme. The in situ yield of (3) is 89.8%

B. Isolation

The reaction mixture is cooled to 5° C. and has a pH of 6.65. Anthraquinone-1,5-disulfonic acid 2 Na (72.3% purity, 10 mmol) is added and the mixture is stirred for 5 minutes. The temperature of the mixture is 4° C. and has a pH of 6.72. Concentrated HCl (2.3 ml) is added resulting in a pH of 2.4, and the mixture is seeded with cefaclor/anthraquinone-1,5-disulfonic acid salt. The mixture is stirred further for 2 minutes and the pH is 3.3. Concentrated HCl (3.9 ml) is added and the pH of the mixture is 1.5. The mixture is stirred for another 30 minutes and has a temperature of 1° C. and a pH of 1.4. The solid precipitate is filtered and washed with 75 ml $H_2O$, then 50 ml of acetone. The filtrate contains phenylglycine, and compounds (1) and (2). The precipitate, the 2:1 salt of (3) and anthraquinone-1,5-disulfonic acid contains 99.8% of the in situ amount of (3).

Example 2

Isolation of Cefaclor as DMF Solvate

Placed the cefaclor/anthraquinone 1,5-disulfonic acid salt (11.06/18.5 mmol) in a 250 ml beaker and added 123 ml of an 85/15 solution of DMF/ H₂O. The pH was 3.85. The mixture was seeded with cefaclor/acid salt and triethylamine was added over a 15 minute period to result in a pH of about 5.7. The mixture was cooled to 18° C., triethylamine was added, and the mixture was stirred and temperature maintained at about 20° C. The mixture was filtered and the solid washed with 35 ml of an 85/15 solution of DMF/ H₂O and then 20 ml of acetone, followed by drying of the solid in a vacuum at 30° C.

Example 3

Formation of Cefaclor Monohydrate

The cefaclor solvate from Example 2 was added to a solution containing 39 ml of H₂O, 0.07 grams of sodium ethylenediaminetetracetic acid, in 1.88 ml of concentrated hydrochloric acid which was precooled to a temperature of between 15°-20° C. Concentrated hydrochloride acid was added, followed by triethylamine. The mixture was seeded with cefaclor monohydrate and stirred. Triethylamine was added as necessary and the mixture was cooled to 0°-5° C. and stirred. Thereafter, the mixture was filtered and the solid was washed with 20 ml of cooled H₂O. The solid was allowed to air dry in a hood, resulting in cefaclor monohydrate.

I claim:

1. A process for the isolation of cefaclor or salt thereof from an acylation reaction mixture, which comprises the step of adding anthraquinone-1,5-disulfonic acid or an alkali metal salt thereof to said mixture to form the 2:1 cefaclor/anthraquinone-1,5-disulfonic acid salt.

2. The process as recited in claim 1 wherein said acylation reaction mixture comprises a compound of the formula

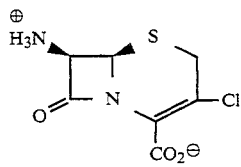

3. The process as recited in claim 2 wherein said acylation reaction mixture comprises phenylglycine or salt thereof.

4. The process as recited in claim 3 wherein said acylation reaction mixture comprises D-phenylglycine methylester or salt thereof.

5. The process as recited in claim 1 wherein said anthraquinone-1,5-disulfonic acid is added in an amount of between about 0.5 moles to about 2 moles per mole of cefaclor.

6. The process as recited in claim 1 wherein the addition step is carried out at a pH of about 1.0 to 4.0, and a temperature of about 0° to about 25° C.

7. The process as recited in claim 1, further comprising the step of isolating said cefaclor/anthraquinone disulfonic acid salt.

8. The process as recited in claim 5 wherein the acid is added in an amount of between about 0.5 to about 0.7 moles per mole of cefaclor.

9. The process as recited in claim 6 wherein the pH is between about 1.3 and about 1.7, and the temperature is between 0° and 10° C.

* * * * *